US012736533B2

(12) United States Patent
Farris et al.

(10) Patent No.: US 12,736,533 B2
(45) Date of Patent: Sep. 15, 2026

(54) ANTIBODY TESTS FOR IDENTIFYING RO NEGATIVE SJOGREN'S SYNDROME AND USE AS BIOMARKERS FOR DYSREGULATED B CELL RESPONSES, B CELL LYMPHOMA, TISSUE FIBROSIS AND SALIVARY GLAND DYSFUNCTION

(71) Applicants: Oklahoma Medical Research Foundation, Oklahoma City, OK (US); The Board of Regents of the University of Oklahoma, Norman, OK (US)

(72) Inventors: A. Darise Farris, Edmond, OK (US); Sherri Longobardi, Oklahoma City, OK (US)

(73) Assignees: Oklahoma Medical Research Foundation, Oklahoma City, OK (US); The Board of Regents of the University of Oklahoma, Norman, OK (US)

( * ) Notice: Subject to any disclaimer, the term of this patent is extended or adjusted under 35 U.S.C. 154(b) by 1078 days.

(21) Appl. No.: 17/797,619

(22) PCT Filed: Feb. 4, 2021

(86) PCT No.: PCT/US2021/016596
§ 371 (c)(1),
(2) Date: Aug. 4, 2022

(87) PCT Pub. No.: WO2021/158779
PCT Pub. Date: Aug. 12, 2021

(65) Prior Publication Data

US 2023/0152313 A1 May 18, 2023

Related U.S. Application Data

(60) Provisional application No. 63/110,476, filed on Nov. 6, 2020, provisional application No. 62/970,043, filed on Feb. 4, 2020.

(51) Int. Cl.
*G01N 33/564* (2006.01)

(52) U.S. Cl.
CPC ..... *G01N 33/564* (2013.01); *G01N 2800/101* (2013.01); *G01N 2800/52* (2013.01)

(58) Field of Classification Search
CPC .......... G01N 33/564; G01N 2800/101; G01N 2800/52; G01N 33/6854
See application file for complete search history.

(56) References Cited

U.S. PATENT DOCUMENTS

2014/0162282 A1 6/2014 Schafer et al.

FOREIGN PATENT DOCUMENTS

WO WO-2010053772 A2 * 5/2010 ............ C07K 16/30
WO WO2018215400 * 11/2018 ....... G01N 2800/065

OTHER PUBLICATIONS

Han et al., PLoS One, 7(2): e32383, (Year: 2012).*
(Continued)

*Primary Examiner* — Stacey N Macfarlane
(74) *Attorney, Agent, or Firm* — Edwin S. Flores; Daniel J. Chalker; Chalker Flores, LLP

(57) ABSTRACT

The present invention includes a method and kit of determining that a patient negative for anti-Ro autoantibodies has Sjögren's syndrome (SS) without performing a lip biopsy comprising: obtaining a liquid biological sample from the patient suspected of having SS: determining that the patient is negative for anti-Ro autoantibodies; and detecting autoantibodies to 1, 2, 3, 4, 5, 6, 7, 8, or 9 proteins selected from: CCDC155, DDB1, MUM1L1, NFU1, RPS29, SOX5, TCP10, ZNF655, or RPAP3, which indicate(s) that the patient has SS. Also, a lack of certain autoantibodies such as KCNAB1, KCNAB2, or as listed in Table 1, Table 2, or Table 3, and FIG. 11 or 16 in Ro neg cases may be used to detect SS.

9 Claims, 10 Drawing Sheets

(56) References Cited

OTHER PUBLICATIONS

Siapka et al., Autoimmunity, 40(3):223-233, (Year: 2007).*
Vivino et al., Rheum Dis Clin North Am, 42(3): 531-551, (Year: 2016).*
Supplementary Partial European Search Report by the European Patent Office for EP 21750408, Mar. 15, 2024, 19 pp.
Anonymous: "HuProt v4.0 Full Content with Sequences" 2024, 1-1.
Anonymous: "HuProt v4.0 Full Content with Sequences" 2019, 1-10.
Hu, et al., "Identification of Novel Biomarkers for Behcet Disease Diagnosis Using Human Proteome Microarray Approach," Molecular & Cellular Proteomics, 2017, pp. 147-156.
Jeong, Jun Seop, et al., "Rapid Identification of Monospecific Monoclonal Antibodies Using a Human Proteome Microarray," Molecular & Cellular Proteomics 16.2, 2012, 10 pp.
Edwards, SK, et al., "Expression and function of a novel isoform of Sox5 in malignant B cells," Leuk Res., Mar. 2014, 38(3), pp. 393-401.
Fox, RI, et al., "Pathogenesis of Sjogren's syndrome," Sjogren's Syndrome chapter, Rheum Dis Clin North Am vol. 18, No. 3, pp. 517-538.
Guan Z, et al., "Expression patterns of genes critical for SHH, BMP, and FGF pathways during the lumen formation of human salivary glands," J Mol Histol, Jan. 2019, vol. 50:217-227.
International Search Report and Written Opinion for PCT/US2021/016596 dated Jun. 25, 2021, 14 pp.
Jin, et al., "Systemic Sclerosis is a complex disease associated mainly with immune regulatory and inflammatory genes," The Open Rheumatology Journal, 2014, vol. 8, pp. 29-42.
Jonsson MV, et al., "Serological implications of germinal center-like structures in primary Sjogren's syndrome," J Rheumatol, 2007, vol. 34, pp. 2044-2049.
Leehan KM, et al., "Minor salivary gland fibrosis in Sjogren's syndrome is elevated, associated with focus score and not solely a consequence of aging," Clin Exp Rheumatol., May-Jun. 2018;36 Suppl 112(3):80-88. Epub Oct. 23, 2017, 2018.
Lessard CJ, et al. 2013, "Variants at multiple loci implicated in both innate and adaptive immune responses are associated with Sjogren's syndrome," Nature Genetics, Nov. 2013, vol. 45(11), pp. 1284-1292.
Maier-Moore, JS, et al., "Antibody-secreting cell specificity in labial salivary glands reflects clinical presentation and serology in Sjogren's syndrome patients," Arthritis Rheumatol, Dec. 2014, vol. 66(12):3445-56.
Mingueneau M, et al., "Cytometry by time-of-flight immunophenotyping identifies a blood Sjogren's signature correlating with disease activity and glandular inflammation," J Allergy Clin Immunol, Jan. 2016, 137:1809-1821.
Park, et al., "Distinct clinical characteristics of anti-Ro/SSA-negative primary Sjogren's syndrome: Data from a nationalwide cohort for Sjogren's syndrome in Korea," Clinical and Experimental Rheumatology, 2019, Abstract, p. 108.
Pei XH, et al., "Sox5 induces epithelial to mesenchymal transition by transactivation of Twist1," Biochem Biophys Res Commun 446:322-327.
Rakhmanov M, et al., "High levels of SOX5 decrease proliferative capacity of human B cells, but permit plasmablast differentiation" PLoS One, Jun. 2014, vol. 9, Issue 6, :e100328, 12 pp.
Ramos-Casals M, et al., "Primary Sjogren's syndrome: new clinical and therapeutic concepts," Ann Rheum Dis , 2005, vol. 64:347-354.
Shiboski CH, et al., "2016 American College of Rheumatology/European League Against Rheumatism Classification Criteria for Primary Sjogren's Syndrome: A Consensus and Data-Driven Methodology Involving Three International Patient Cohorts," Arthritis Rheumatol Jan. 2017, vol. 69(1) pp. 35-45.
Shiboski CH, et al., "2016 American College of Rheumatology/European League Against Rheumatism classification criteria for primary Sjogren's syndrome: A consensus and data-driven methodology involving three international patient cohorts," Ann Rheum Dis 76:9-16.
Siapka, et al., "Multiple specificities of autoantibodies against hnRNP A/B proteins in systemic rheumatic diseases and hnRNP L as an associated novel autoantigen," Autoimmunity, May 2007, vol. 40, No. 3, pp. 223-233.
Yin H, et al., "Association of bone morphogenetic protein 6 with exocrine gland dysfunction in patients with Sjogren's syndrome and in mice," Arthritis Rheum Dec. 2013, 65(12), pp. 3228-3238.
Zhang D, "SOX5 promotes epithelial-mesenchymal transition in osteosarcoma via regulation of Snail," JBUON, 2017, vol. 22(1), pp. 258-264.

* cited by examiner

| | | | | | | | | | | | | |
|---|---|---|---|---|---|---|---|---|---|---|---|---|
| p1031866.1_RoNeg | | | SOX5 | | | | | | | | | |
| p1034387.0_RoNeg | | | SOX5 | SOX6 | | | | SOX11 | | | | |
| p1033665.7_RoPos | | | SOX5 | SOX6 | | | | SOX11 | SOX13 | | | |
| p1034478.2_RoNeg | | | SOX5 | SOX6 | | | | | SOX13 | | | |
| p1033675.3_RoPos | | | SOX5 | SOX6 | | | | | SOX13 | SOX17 | | |
| p1033540.3_RoPos | | | SOX5 | SOX6 | | | | | | SOX17 | | |
| p1034329.0_RoNeg | | | SOX5 | SOX6 | | SOX9 | | | SOX13 | | | |
| p1033198.5_RoPos | | | SOX5 | SOX6 | SOX8 | SOX9 | | | SOX13 | | | |
| p1033623.4_RoPos | | | SOX5 | SOX6 | SOX8 | SOX9 | | | SOX13 | | | |
| p1033210.4_RoPos | | | SOX5 | SOX6 | SOX8 | SOX9 | | | | | | |
| p1033215.8_RoPos | | | SOX5 | SOX6 | | SOX9 | SOX10 | | SOX13 | | | |
| p1035809.4_RoNeg | SOX3 | SOX4 | SOX5 | SOX6 | | | | | SOX13 | | | |
| p1034279.6_RoNeg | SOX3 | | SOX5 | | | | | SOX11 | | | | SOX30 |
| p1031784.2_RoPos | SOX3 | | | SOX6 | | | | | | | SOX18 | |

ANTIBODY TESTS FOR IDENTIFYING RO NEGATIVE SJOGREN'S SYNDROME AND USE AS BIOMARKERS FOR DYSREGULATED B CELL RESPONSES, B CELL LYMPHOMA, TISSUE FIBROSIS AND SALIVARY GLAND DYSFUNCTION

CROSS-REFERENCE TO RELATED APPLICATIONS

This application is a National Stage of International Application of PCT/US2021/016596, filed Feb. 4, 2021, which claims the benefit of U.S. Provisional Application No. 62/970,043, filed Feb. 4, 2020 and U.S. Provisional Application Ser. No. 63/110,476 filed Nov. 6, 2020, the entire contents of which is incorporated herein by reference.

STATEMENT OF FEDERALLY FUNDED RESEARCH

This invention was made with government support under 1R01AR074310-02 awarded by the National Institutes of Health. The government has certain rights in the invention.

TECHNICAL FIELD OF THE INVENTION

The present invention relates in general to the field of novel antibody tests for identifying Ro negative Sjögren's Syndrome and use as biomarkers for dysregulated B cell responses, B cell lymphoma, tissue fibrosis and salivary gland dysfunction.

BACKGROUND OF THE INVENTION

Without limiting the scope of the invention, its background is described in connection with Sjögren's Syndrome.

Sjögren's syndrome (SS) is a rheumatic autoimmune disease selectively targeting salivary and lacrimal glands, leading to painful dry mouth and eyes, oral infections, severe dental caries/tooth loss, fatigue, arthritis, nervous system involvement and malignant B cell lymphoma. Current internationally accepted disease classification criteria rely on either the presence of anti-Ro antibodies (these may target either the Ro60 antigen, Ro52 antigen or both) or the presence of focal lymphocytic infiltrates in a minor salivary gland lip biopsy for diagnosis (1, 2).

Among 475 individuals attending the Oklahoma Sjögren's Research clinic and meeting classification criteria for primary SS, 38% lacked antibodies to Ro antigen. These individuals met classification criteria for SS due to a focus score ≥1 on examination of minor salivary gland lip biopsy. The antigen(s) driving the aberrant immune response in these individuals is unknown.

Novel methods are needed for identifying anti-Ro antibody negative patients with SS, but without the need to perform a salivary gland lip biopsy.

SUMMARY OF THE INVENTION

In one embodiment, the present invention includes a method of determining that a patient negative for Ro autoantibodies has Sjögren's syndrome (SS) with or without performing a lip biopsy comprising: obtaining a biological sample from the patient: detecting if the biological sample has autoantibodies to 1, 2, 3, 4, 5, 6, 7, 8, 9, 10, 11, 12, 13, 14, 15, 16, 17, 18, 19, 20, 21, 22, 23, 24, or 25 proteins selected from their encoding gene names: RPAP3, ARFGAP1, C9orf78, CNDP2, FABP1, FXYD5, GRAMD1A, HNRNPAB, LIX1, MCCC2, PEAS/ND, POU6F1, PPIL3, SPSB2, SRPK2, WDR20, CCDC155, DDB1, MUM1L1, NFU1, RPS29, SOX5, TCP10, ZNF655, or RPAP3 wherein the level of autoantibody is ≥3 standard deviations (SD) above the mean of healthy controls. In one aspect, the method further comprises the step of detecting if the biological sample has autoantibodies to at least one of: CCDC155, DDB1, MUM1L1, NFU1, RPS29, SOX5, TCP10, ZNF655, or RPAP3 from a Ro positive or Ro negative patient and determining that the patient has SS without performing a lip biopsy. In another aspect, the autoantibody has a reactivity of ≥4SD above the mean of healthy controls to at least one of: RPAP3, MUM1L1, RPS29, SOX5 or RPAP3 to identify three-fourths of the Ro negative individuals with SS. In another aspect, the method further comprises the step of detecting if the biological sample has autoantibodies to at least one of: CCDC155, DDB1, MUM1L1, NFU1, RPS29, SOX5, TCP10, ZNF655, or RPAP3, identifies 93% of the Ro positive cases and 87% of the Ro negative cases. In another aspect, the autoantibodies to SOX5 also cross-react with at least one of SOX3, SOX4, SOX6, SOX9, SOX11, SOX13 and SOX30. In another aspect, the method further comprises the step of detecting if the liquid biological sample has autoantibodies to one or more proteins in Table 1, other than MUM1L1 and SOX5. In another aspect, the method further comprises the step of detecting if the liquid biological sample has autoantibodies to one or more proteins in Table 2 from patients with or without Ro autoantibodies. In another aspect, the autoantibodies are detected using an assay selected from at least one of: ELISA, flow cytometry, fluorimetry, microscopy, immunofluorescence, radioimmunoassay, immunoenzymatic assay, fluorescence activated cell sorting (FACS), differential display, representational difference analysis, microarray. Western blotting, immunohistochemical staining, immunocytochemical staining, dot blots, or surface plasmon resonance detection. In another aspect, the liquid biological sample selected from a saliva, a blood, a plasma, a serum, or a tear sample. In another aspect, the method further comprises the step of treating the patient negative for Ro autoantibodies with a therapy that treats or reduces the symptoms of SS. In another aspect, the biological sample is negative for autoantibodies to KCNAB1, KCNAB2, or as listed in Table 1, Table 2. FIG. 11, or FIG. 16 in Ro negative cases are used to detect SS.

In another embodiment, the present invention includes an assay for detecting autoantibodies to RNA Polymerase II Associated Protein 3 (RPAP3) comprising: contacting a biological sample suspected of having autoantibodies with an RPAP3 protein under conditions in which the presence of autoantibodies to RNA Polymerase II Associated Protein 3 (RPAP3) are detected. In one aspect, the assay is an ELISA, flow cytometry, fluorimetry, microscopy, immunofluorescence, radioimmunoassay, immunoenzymatic assay, fluorescence activated cell sorting (FACS), differential display, representational difference analysis, microarray, Western blotting, immunohistochemical staining, and immunocytochemical staining, dot blots, or surface plasmon resonance detection. In another aspect, the biological sample is a liquid biological sample selected from a saliva, a blood, a serum, a plasma, or a tear sample. In another aspect, the assay further comprises detecting autoantibodies to at least 1, 2, 3, 4, 5, 6, 7 or 8 proteins selected from: CCDC155, DDB1, MUM1L1, NFU1, RPS29, SOX5, TCP10, or ZNF655 antigens. In another aspect, the autoantibody has a reactivity ≥2SD, ≥3SD, or ≥4SD, above the mean of healthy controls to at least one of: CCDC155, DDB1. MUM1L1, NFU1, RPS29, SOX5, TCP10, ZNF655 antigens in the Ro negative group to identify three-fourths of the Ro negative individuals. In another aspect, the autoantibodies to SOX5 also cross-react with at least one of SOX3, SOX4, SOX6, SOX9, SOX11, SOX13 and SOX30. In another aspect, the biological sample is negative for autoantibodies to KCNAB1, KCNAB2, or as listed in Table 1, Table 2, FIG. 11, or FIG. 16 in Ro neg cases are used to detect SS.

In another embodiment, the present invention includes a kit comprising a synthetic or recombinant polypeptide covalently attached to a solid support, wherein the synthetic or recombinant polypeptide comprises 1, 2, 3, 4, 5, 6, 7, 8, or 9 proteins selected from: CCDC155, 30) DDB1, MUM1L1, NFU1, RPS29, SOX5, TCP10, ZNF655, or RPAP3. In one aspect, the kit further comprises instructions for contacting the solid support with a biological sample from a patient suspected of having Sjögren's syndrome. In one aspect, the solid support is selected from the group consisting of a multiwell plate, an enzyme-linked immunosorbent assay (ELISA) plate, a microarray, a bead, a porous strip, and a nitrocellulose filter. In another aspect, the kit is an assay selected from the group consisting of a Western blot, an ELISA, a radioimmunoassay (MA), an immunoprecipitation assay, an electrochemiluminescence assay, a chemiluminescence assay, a fluorescence assay, a microarray, a multiplex bead-based assay, a dot blot, or a surface plasmon resonance detection. In another aspect, the kit further comprises a secondary antibody labeled directly or indirectly with a detectable moiety. In another aspect, the one or more synthetic or recombinant polypeptides further comprise one or more proteins selected from the group consisting of 2, 3, 4, 5, 6, 7 or 8 proteins selected from: CCDC155, DDB1, MUM1L1, NFU1, RPS29, SOX5, TCP10, or ZNF655, or RPAP3.

In another aspect, the kit further comprises reagents for detecting if the liquid biological sample has autoantibodies to one or more proteins in Table 1, Table 2, or Table 3, other than MUM1L1 and SOX5.

In another embodiment, the present invention includes a method of determining that a patient negative for Ro autoantibodies has Sjögren's syndrome (SS) without performing a lip biopsy comprising: obtaining a liquid biological sample from the patient suspected of having SS: determining that the patient is negative for Ro autoantibodies; and detecting autoantibodies to 1, 2, 3, 4, 5, 6, 7, 8, or 9) proteins selected from: CCDC155, DDB1. MUM1L1, NFU1, RPS29, SOX5, TCP10, ZNF655, or RPAP3, in the liquid sample, wherein the present of autoantibodies indicates that the patient has SS. In one aspect, the method further comprises the step of detecting if the liquid biological sample has autoantibodies to 2, 3, 4, 5, 6, 7, 8, or 9 proteins selected from: CCDC155, DDB1, MUM1L1, NFU1. RPS29, SOX5, TCP10. ZNF655, or RPAP3. In one aspect, the autoantibody has a reactivity ≥2SD, ≥3SD, or ≥4SD above the mean of healthy controls to any one of any one of CCDC155, DDB1, MUM1L1, NFU1, RPS29, SOX5, TCP10, ZNF655 antigens in the Ro negative group to identify three-fourths of the Ro negative individuals. In another aspect, the autoantibodies to SOX5 also cross-react with at least one of SOX3, SOX4, SOX6, SOX9, SOX11, SOX13 and SOX30. In another aspect, the method further comprises the step of detecting if the liquid biological sample has autoantibodies to one or more proteins in Table 1, Table 2, or Table 3, other than MUM1L1 and SOX5. In another aspect, the step of detecting autoantibodies in an assay selected from the group consisting of a Western blot, an ELISA, a radioimmunoassay (MA), an immunoprecipitation assay, an electrochemiluminescence assay, a chemiluminescence assay, a fluorescence assay, a microarray, a multiplex bead-based assay, a dot blot, or a surface plasmon resonance detection.

In another embodiment, the present invention includes a method of determining that a patient negative for Ro autoantibodies has Sjögren's syndrome (SS) without performing a lip biopsy comprising: obtaining a liquid biological sample from the patient suspected of having SS: determining that the patient is negative for Ro autoantibodies; and detecting autoantibodies 1, 2, 3, 4, 5, 6, 7, 8, or 9 proteins selected from: CCDC155, DDB1, MUM1L1, NFU1, RPS29, SOX5, TCP10, ZNF655, or RPAP3, wherein the present of autoantibodies to RPAP3 indicates that the patient has SS.

In another embodiment, the present invention includes a kit comprising a synthetic or recombinant polypeptide covalently attached to a solid support, wherein the synthetic or recombinant polypeptide comprises 1, 2, 3, 4, 5, 6, 7, 8, or 9) proteins selected from: CCDC155, DDB1, MUM1L1, NFU1, RPS29, SOX5, TCP10, ZNF655, or RPAP3, and reagents to detect autoantibodies to the 1, 2, 3, 4, 5, 6, 7, 8, or 9 proteins selected from: CCDC155, DDB1, MUM1L1, NFU1, RPS29, SOX5, TCP10, ZNF655, or RPAP3. In one aspect, the kit further comprises instructions for contacting the solid support with a biological sample from a patient suspected of having Sjögren's syndrome. In one aspect, the solid support is selected from the group consisting of a multiwell plate, an enzyme-linked immunosorbent assay (ELISA) plate, a microarray, a bead, a porous strip, and a nitrocellulose filter. In another aspect, the kit is an assay selected from the group consisting of a Western blot, an ELISA, a radioimmunoassay (MA), an immunoprecipitation assay, an electrochemiluminescence assay, a chemiluminescence assay, a fluorescence assay, a microarray, a multiplex bead-based assay, a dot blot, or a surface plasmon resonance detection. In another aspect, the kit further comprises a secondary antibody labeled directly or indirectly with a detectable moiety. In another aspect, the kit further comprises reagents for detecting if the liquid biological sample has autoantibodies to one or more proteins in Table 1, other than MUM1L1 and SOX5.

BRIEF DESCRIPTION OF THE DRAWINGS

For a more complete understanding of the features and advantages of the present invention, reference is now made to the detailed description of the invention along with the accompanying figures and in which:

FIG. 9 is a table that shows that multiple SOX family members are bound by plasma IgG antibodies of individual SS cases in the anti-Ro negative and anti-Ro positive groups above the healthy controls. Positive binding is color-coded by the threshold of positivity used, where 2SD (green) is binding above the mean of the controls plus 2SD, 3SD (yellow) is binding above the mean of healthy controls plus 3SD, and 4SD (red) is binding above the mean of healthy controls plus 4SD. Each row represents binding data by an individual SS patient.

DETAILED DESCRIPTION OF THE INVENTION

Figure 1:
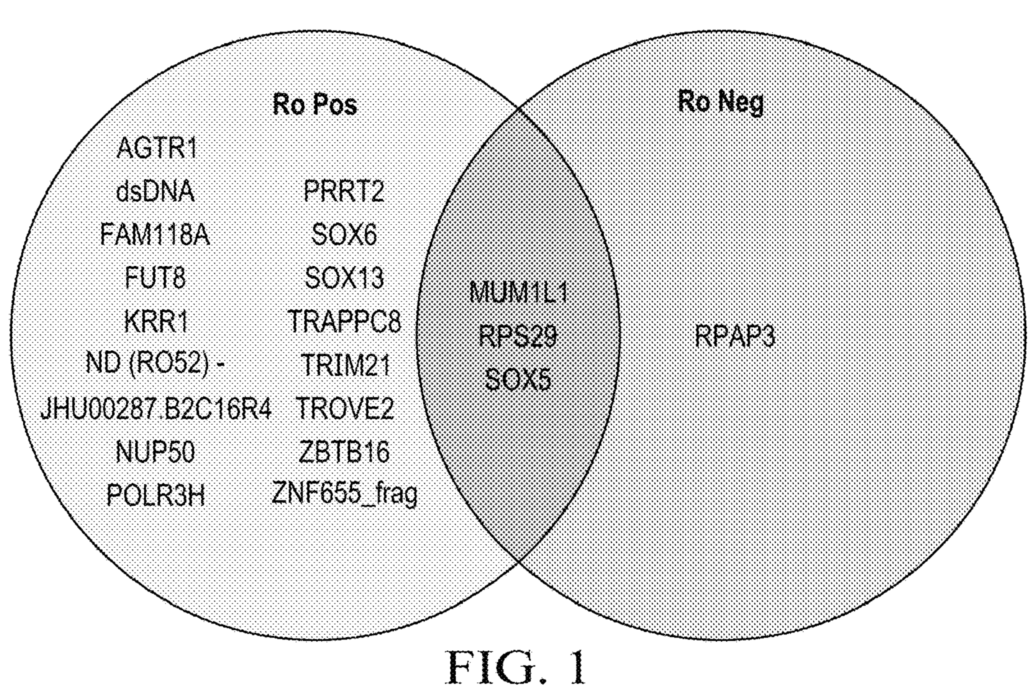
FIG. 1 shows the antigens identified on HuProt3.2 arrays that were bound by anti-Ro antibody positive SS patients (Ro Pos, n=15)) or anti-Ro antibody negative SS patients (Ro Neg, n=15) compared to matched healthy controls (n=15). Positive binding was defined as normalized and background-corrected intensity values ≥4SD above the mean of healthy controls. The antigens shown showed significant differences from the healthy control group by Fisher's exact test.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but include the general class of which a specific example may be used for illustration. The terminology herein is used to describe specific embodiments of the invention, but their usage does not limit the invention, except as outlined in the claims.

The present invention is used for the diagnosis of Ro antibody negative Sjögren's syndrome (SS) without a minor salivary gland lip biopsy. Thus, the present invention allows for the first time the diagnosis of Ro antibody negative Sjögren's syndrome without a minor salivary gland lip biopsy.

The present invention also teaches biomarker(s) of dysregulated B cell responses, B cell lymphoma, salivary gland fibrosis and/or salivary gland dysfunction.

Diagnosis of SS in individuals lacking antibodies to Ro antigen currently requires observation of focal lymphocytic infiltrates on salivary gland lip biopsy. The inventors have discovered antigens recognized by antibodies in "Ro negative" SS patients. This discovery permits diagnosis and/or treatment of SS without a lip biopsy.

SS is a rheumatic autoimmune disease selectively targeting salivary and lacrimal glands, leading to painful dry mouth and eyes, oral infections, severe dental caries/tooth loss, fatigue, arthritis, nervous system involvement and malignant B cell lymphoma. Current internationally accepted disease classification criteria rely on either the presence of anti-Ro antibodies (these may target either the Ro60) antigen, Ro52 antigen or both) or the presence of focal lymphocytic infiltrates in a salivary gland lip biopsy for diagnosis (1, 2). Either one of these features, in combination with one or more objective dryness measures are necessary for fulfillment of classification criteria for SS.

Among 475 individuals attending the Oklahoma Sjögren's Research clinic and meeting classification criteria for primary SS, 38% lacked antibodies to Ro antigen. These individuals met classification criteria for SS due to a focus score ≥1 on examination of salivary gland lip biopsy. The antigen(s) driving the aberrant immune response in these individuals is unknown. The inventors' prior published (3) and unpublished (Longobardi and Farris, unpublished data) work shows that many of the antigens recognized by monoclonal antibodies derived from salivary gland antibody-forming plasmablasts are also present in plasma, serum or saliva. However, what is needed are novel methods for detecting SS patients that are Ro antigen negative.

To discover novel autoantigens in Ro antibody negative SS cases, the inventors tested plasma from Ro negative SS cases (n=15), Ro positive SS cases (n=15) and healthy controls (n=15) for binding to more than 15,500 antigens using human proteome microarrays (HuProt3.2, CDI Laboratories). All groups were matched on age within 5 years, race and sex. The arrays were probed with 1:500 dilutions of plasma and signals detected using a fluorescently labeled anti-human IgG secondary antibody (Jackson ImmunoResearch AlexaFluor647 AffiniPure F(ab)2 Fragment Goat Anti-Human IgG (H+L), cat #109-606-003 at 1:2000 dilution). After scanning fluorescent signals using a GenePix scanner, the arrays were probed with an anti-GST antibody, which captured signals for all proteins, as all proteins on the array carry a GST tag. Each array was manually aligned using GST signals. Manual analysis of the foreground/background ratio of GST signals of one representative array probed with anti-GST antibody alone was used to assess adequate presence of each protein in each set of duplicate spots. This analysis revealed no instance of protein being present on only one spot on the array. Using the Protein Array Analyzer (PAA) Bioconductor open source software in R, all 45 arrays were normalized to one another using robust linear model (rlm) normalization. Of the duplicate spots of each protein, the protein exhibiting the lower signal was selected for analysis. Appropriate normalization was verified by the observation of equalized positive immunoglobulin light chain spots present on each array, as these proteins should be identically detected using the fluorescently labeled anti-human IgG reagent employed. The PAA background correction feature was employed to correct for intra-array fluctuations in background. The normalized and background-corrected data were analyzed using two methods.

Using the first analysis method, the average #4 SD of the healthy control group was computed for each protein. The patient groups were evaluated for antigens that: (i) bound greater than the average+4SD above the healthy control group and: (ii) exhibited significant differences between either anti-Ro antibody negative or anti-Ro antibody positive cases versus healthy controls by a Fisher's exact test. Using these criteria, four novel antigens were significantly bound by the anti-Ro negative SS group, while 19 antigens were significantly bound by the anti-Ro positive SS group (FIG. 1). Among these antigens, three novel antigens were bound by individuals in both patient groups but not the healthy control group. These antigens were listed on the CDI human proteome arrays as MUM1L1, RPS29 and SOX5. One novel antigen was uniquely bound by the anti-Ro negative group compared to healthy controls. This antigen was listed on the CDI human proteome arrays as RPAP3. Notably, reactivity ≥4SD above the mean of healthy controls to any one of the four novel antigens in the Ro negative group could identify nearly three-fourths of the Ro negative individuals (positive predictive value=73.3%, negative predictive value=100%). Antigens bound by antibodies in the anti-Ro positive group included the known canonical antigens Ro60 (identified on the HuProt3.2 arrays as TROVE2) and Ro52 (identified on the HuProt3.2 arrays as TRIM21 and as ND JHU00287.B2C16R4), validating the approach and analysis methods. Additional antigens identified in the anti-Ro positive group are also novel and are being explored as biomarkers for clinical and histological disease features.

FIG. 1 shows the antigens identified on HuProt3.2 arrays that were bound by anti-Ro positive SS patients (Ro Pos, n=15) or anti-Ro negative SS patients (Ro Neg. n=15) compared to matched healthy controls (n=15). Positive binding was defined as normalized and background-corrected intensity values ≥4SD above the mean of healthy controls. The antigens shown showed significant differences from the healthy control group by Fisher's exact test.

To further demonstrate the magnitude of the responses to the novel antigens bound by the anti-Ro negative group, the normalized and background-corrected intensity values of the antigen binding in all three groups were plotted (FIGS. 2-5). Two-way comparisons between each SS group and the healthy control group were made using the Mann-Whitney U test, and the resulting p-values are shown in each figure.

Figure 2:
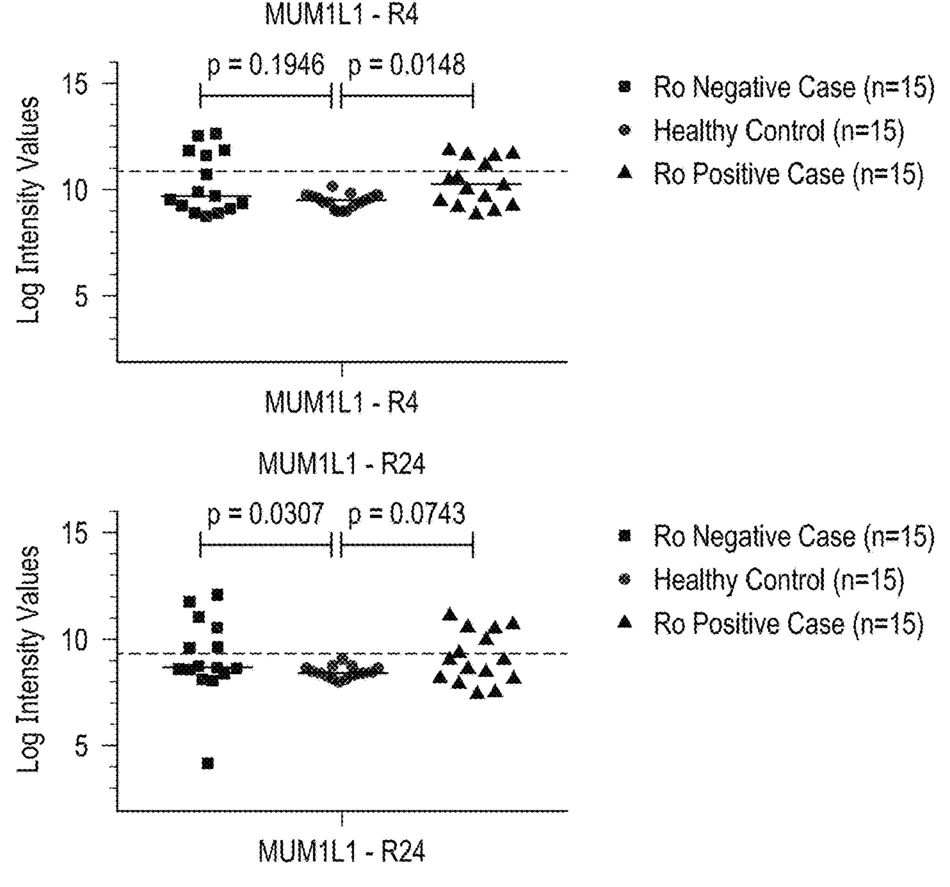
FIG. 2 is a graph that shows binding of two versions of MUM1L1 protein by both anti-Ro negative SS cases (squares, left) and anti-Ro positive SS cases (triangles, right) but not matched healthy controls (circles, center). Red dashed lines indicate threshold of 4SD above the mean of the healthy control group. P-values using one-tailed Mann-Whitney U test compared to the healthy control group are shown.

FIG. 2 is a graph that shows binding of two versions of MUM1L1 protein by both anti-Ro negative SS cases (squares, left) and anti-Ro positive SS cases (triangles, right) but not matched healthy controls (circles, center). Red dashed lines indicate the threshold of 4SD above the mean of the healthy control group. P-values using one-tailed Mann-Whitney U test compared to the healthy control group are shown.

Figure 3:
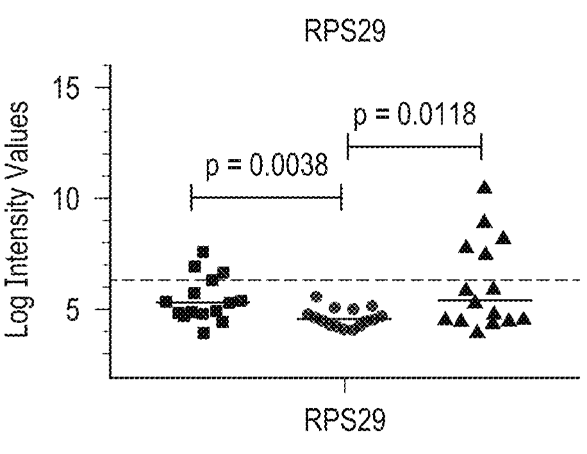
FIG. 3 is a graph that shows binding of RPS29 protein by both anti-Ro negative SS cases (squares, left) and anti-Ro positive SS cases (triangles, right) but not matched healthy controls (circles, center). Red dashed line indicates threshold of 4SD above the mean of the healthy control group. P-values using one-tailed Mann-Whitney U test compared to the healthy control group are shown.

FIG. 3 is a graph that shows binding of RPS29 protein by both anti-Ro negative SS cases (squares, left) and anti-Ro positive SS cases (triangles, right) but not matched healthy controls (circles, center). Red dashed line indicates the threshold of 4SD above the mean of the healthy control group. P-values using one-tailed Mann-Whitney U test compared to the healthy control group are shown.

Figure 4:
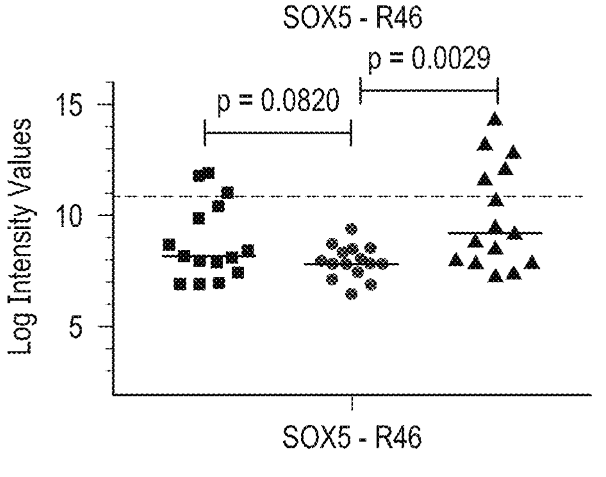
FIG. 4 is a graph that shows binding of two isoforms of SOX5 protein by both anti-Ro negative SS cases (squares, left) and anti-Ro positive SS cases (triangles, right) but not matched healthy controls (circles, center). Red dashed lines indicate threshold of 4SD above the mean of the healthy control group. P-values using one-tailed Mann-Whitney U test compared to the healthy control group are shown.
Figure 4:
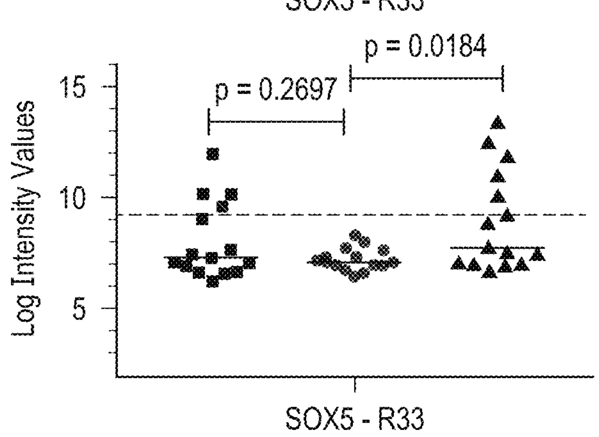

FIG. 4 is a graph that shows binding of two isoforms of SOX5 protein by both anti-Ro negative SS cases (squares, left) and anti-Ro positive SS cases (triangles, right) but not matched healthy controls (circles, center). Red dashed lines indicate the threshold of 4SD above the mean of the healthy control group. P-values using one-tailed Mann-Whitney U test compared to the healthy control group are shown.

Figure 5:
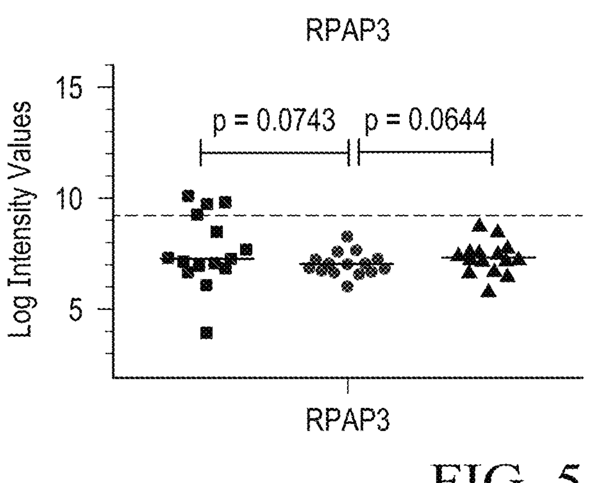
FIG. 5 is a graph that shows binding of RPAP3 protein by anti-Ro negative SS cases (squares, left) but not anti-Ro positive SS cases (triangles, right) or matched healthy controls (circles, center). Red dashed line indicates threshold of 4SD above the mean of the healthy control group. P-values using a one-tailed Mann-Whitney U test compared to the healthy control group are shown.
Figure 5:

FIG. 5 is a graph that shows binding of RPAP3 protein by anti-Ro negative SS cases (squares, left) but not anti-Ro positive SS cases (triangles, right) or matched healthy controls (circles, center). Red dashed line indicates the threshold of 4SD above the mean of the healthy control group. P-values using a one-tailed Mann-Whitney U test compared to the healthy control group are shown.

As three of the novel antigens were bound by individuals in both patient groups, the inventors also evaluated the magnitude of binding by the combined patient groups compared to the healthy control group using the Mann-Whitney U test. These results are shown in FIGS. 6-8.

Figure 6:
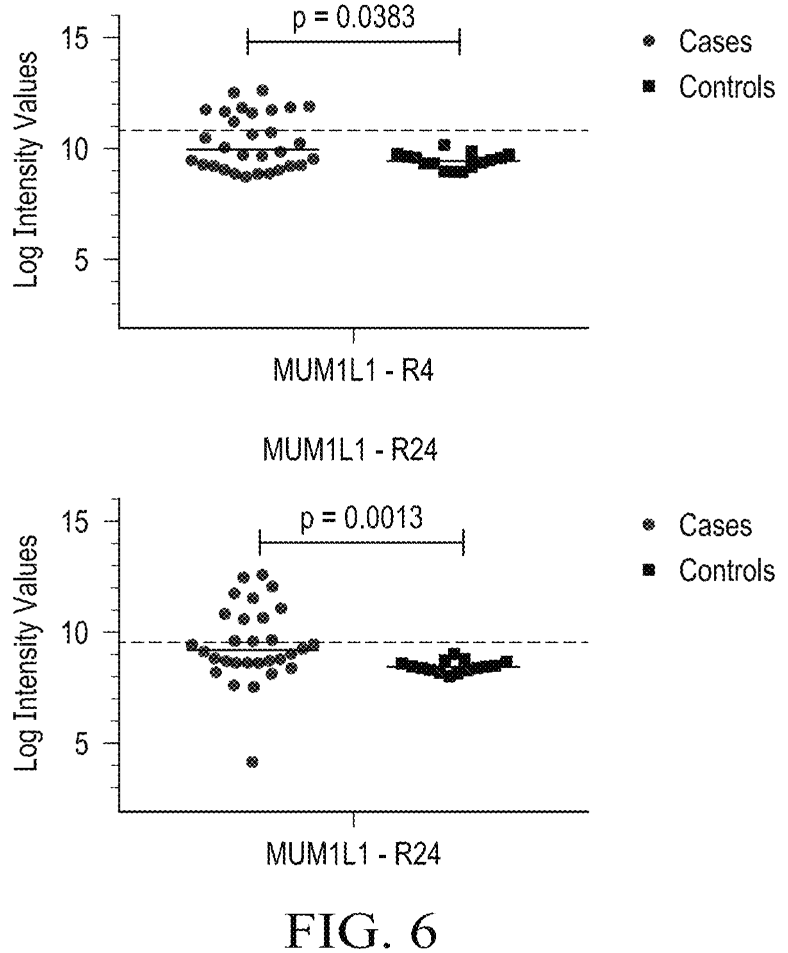
FIG. 6 is a graph that shows binding of two versions of MUM1L1 protein by the combined anti-Ro negative and anti-Ro positive patient groups (n=30, circles, left) but not matched healthy controls (n=15, squares, right). Red dashed lines indicate threshold of 4SD above the mean of the healthy control group. P-values using one-tailed Mann-Whitney U tests compared to the healthy control group are shown.

FIG. 6 is a graph that shows binding of two versions of MUM1L1 protein by the combined anti-Ro negative and anti-Ro positive patient groups (n=30, circles, left) but not matched healthy controls (n=15, squares, right). Red dashed lines indicate the threshold of 4SD above the mean of the healthy control group. P-values using one-tailed Mann-Whitney U tests compared to the healthy control group are shown.

Figure 7:
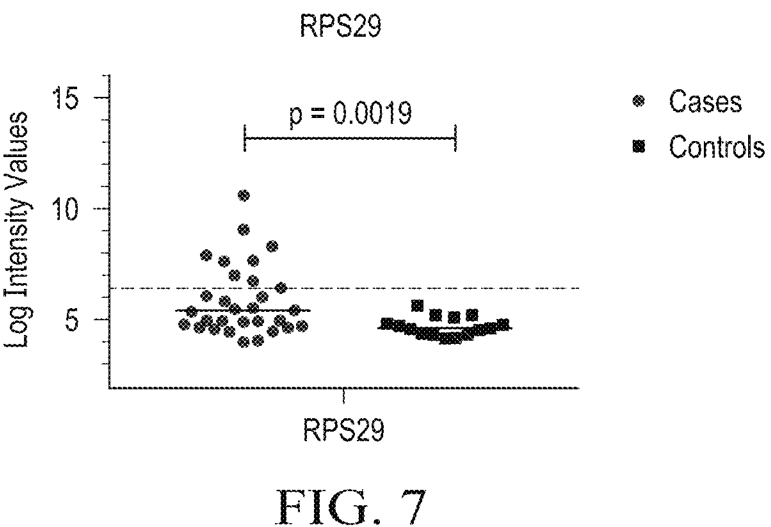
FIG. 7 is a graph that shows binding of the RPS29 protein by the combined anti-Ro negative and anti-Ro positive patient groups (n=30, circles, left) but not matched healthy controls (n=15, squares, right). Red dashed line indicates threshold of 4SD above the mean of the healthy control group. P-value using a one-tailed Mann-Whitney U test compared to the healthy control group is shown.

FIG. 7 is a graph that shows binding of the RPS29 protein by the combined anti-Ro negative and anti-Ro positive patient groups (n=30, circles, left) but not matched healthy controls (n=15, squares, right). Red dashed line indicates threshold of 4SD above the mean of the healthy control group. P-value using a one-tailed Mann-Whitney U test compared to the healthy control group is shown.

Figure 8:
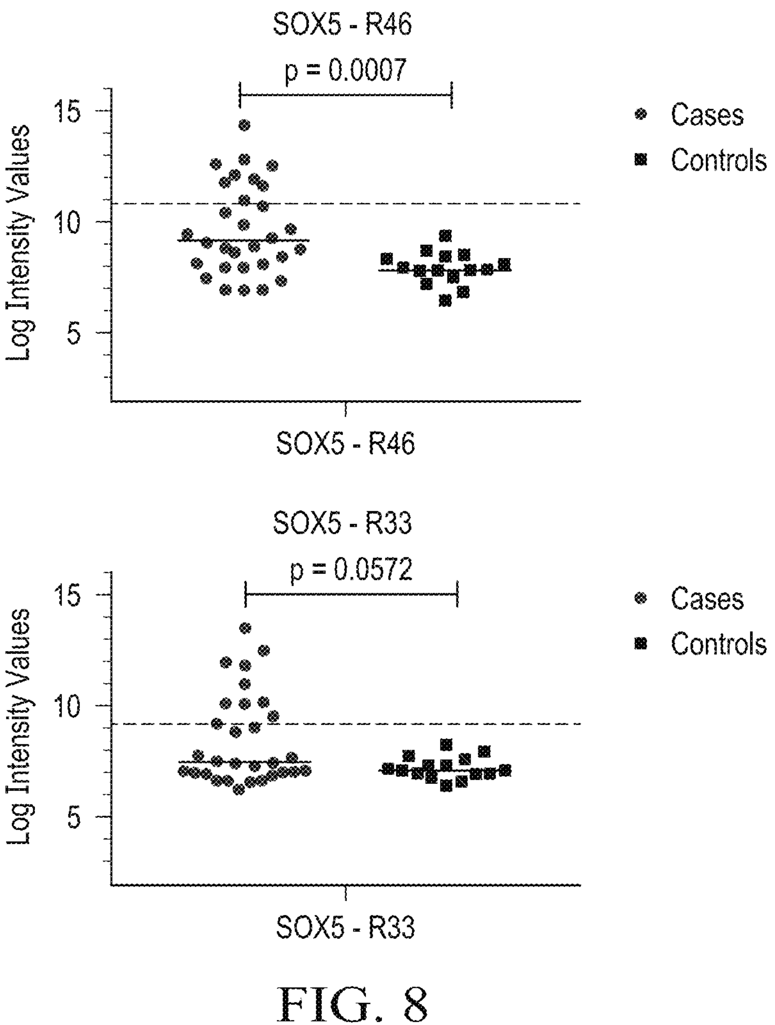
FIG. 8 is a graph that shows binding of two isoforms of SOX5 protein by the combined anti-Ro negative and anti-Ro positive patient groups (n=30, circles, left) but not matched healthy controls (n=15, squares, right). Red dashed lines indicate threshold of 4SD above the mean of the healthy control group. P-values using one-tailed Mann-Whitney U tests compared to the healthy control group are shown.

FIG. 8 is a graph that shows binding of two isoforms of SOX5 protein by the combined anti-Ro negative and anti-Ro positive patient groups (n=30, circles, left) but not matched healthy controls (n=15, squares, right). Red dashed lines indicate threshold of 4SD above the mean of the healthy control group. P-values using one-tailed Mann-Whitney U tests compared to the healthy control group are shown.

As multiple SOX family members were targeted in the anti-Ro positive SS cases, the inventors evaluated binding to all SOX family members present on the proteome arrays using various thresholds of positivity, defined by the mean of healthy controls plus 2SD, 3SD or 4SD. The results showed that plasma IgG from Ro negative cases also bound to SOX3, SOX4, SOX6, SOX9, SOX11, SOX13 and SOX30, in addition to SOX5. Both anti-Ro negative and anti-Ro positive cases could bind to multiple SOX family members (FIG. 9). As folding of protein on the proteome arrays may not be in completely native conformation, these data show that additional SOX family members may be useful for the application of diagnosing Ro negative SS cases.

FIG. 9 is a table that shows that multiple SOX family members are bound by plasma IgG antibodies of individual SS cases in the anti-Ro negative and anti-Ro positive groups above the healthy controls. Positive binding is color-coded by the threshold of positivity used, where 2SD (green) is binding above the mean of the controls plus 2SD, 3SD (yellow) is binding above the mean of healthy controls plus 3SD, and 4SD (red) is binding above the mean of healthy controls plus 4SD. Each row represents binding data by an individual SS patient.

SOX5 has been shown to be expressed in late stage B cell differentiation including atypical memory B cells, germinal center B cells and plasmablasts (4). As ectopic germinal centers are prevalent, and as plasmablasts are numerous in the salivary gland biopsy tissue of SS patients (5, 6), antibodies to SOX5 may be useful as a biomarker for dysregulated B cells occurring in salivary gland, blood or other tissues in SS patients. A biomarker for dysregulated B cell function in SS may be a useful biomarker for determining patient response to therapy, both in clinical trials and in patient care. SOX5 and other SOX family members have been shown to mediate epithelial to mesenchymal cell transition (EMT) (7, 8), a key pathway for promotion of tissue fibrosis. The inventors have shown that tissue fibrosis, as assessed by morphological criteria, is increased in the salivary gland biopsy tissue of SS cases (9). Therefore, antibodies to SOX5 in serum or saliva may be a useful biomarker for salivary gland tissue fibrosis, which could be useful for selecting patients for certain clinical trials or therapies. SOX5 is a marker of malignant B cells (10), and SS patients have a substantially increased risk of malignant B cell lymphoma (11, 12). Therefore, antibodies to SOX5 in SS patient samples may be useful as a biomarker for B cell lymphoma or risk for B cell lymphoma in SS patients. These are novel antigens in SS.

Figure 10:
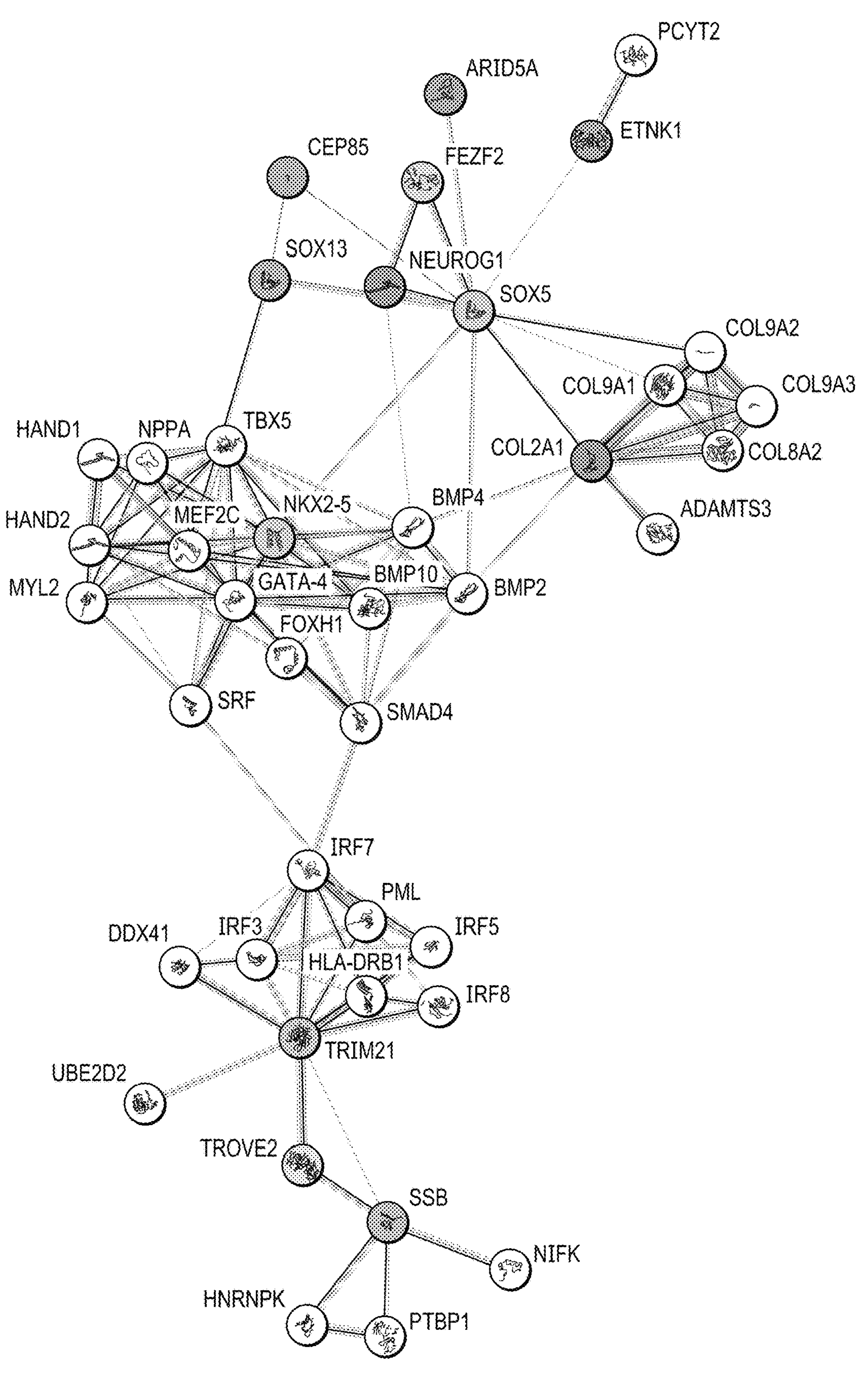
FIG. 10 shows the known and predicted protein-protein interactions involving SOX5 and Ro60 identified by the STRING database. Note close connections of SOX5 and SOX13, connections between SOX proteins, a collagen network, and a TGFbeta family member network. These networks are connected to an innate immune signaling network known to be dysregulated in SS. The latter network is linked to the canonical Ro60 antigen.

Evaluation of protein-protein interactions connecting the SOX5 protein and the canonical Ro60 antigen in SS using the Search Tool for Retrieval of Interacting Genes/Proteins (STRING) database revealed a close relationship between SOX5 and SOX13, which are among the most strongly bound SOX family members in SS (FIG. 10). The analysis also revealed direct interactions between SOX5 and SOX13 to a network of TGFbeta receptor and TGF beta receptor family member signaling, and direct connections between SOX5 and multiple collagen proteins (FIG. 10). TGFbeta signaling and collagen proteins are well known key mediators of tissue fibrosis. Moreover, the TGFbeta receptor signaling family member BMP proteins are involved in salivary gland differentiation and regeneration (13), and at least one BMP protein has been shown to be altered in SS and associated with salivary gland dysfunction in SS (14). Notably, the interactions above are also linked to a network of inflammatory signaling proteins known to be dysregulated in SS (15), as well as the canonical Ro antigens (FIG. 10). These data provide additional evidence that antibodies to SOX family members may be useful as biomarkers for fibrosis and disease activity in SS.

FIG. 10 shows the known and predicted protein-protein interactions involving SOX5 and Ro60 identified by the STRING database. Note close connections of SOX5 and SOX13, connections between SOX proteins, a collagen network, and a TGFbeta family member network. These networks are connected to an innate immune signaling network known to be dysregulated in SS. The latter network is linked to the canonical Ro60 antigen.

A second analysis method available in the PAA Bioconductor R package was also employed to find novel SS antigens that can discriminate SS cases from healthy controls. Using this analysis antibody reactivity to 13 proteins were shown to significantly discriminate between SS cases and healthy controls after adjusting for multiple comparisons (FIG. 11).

Figure 11:
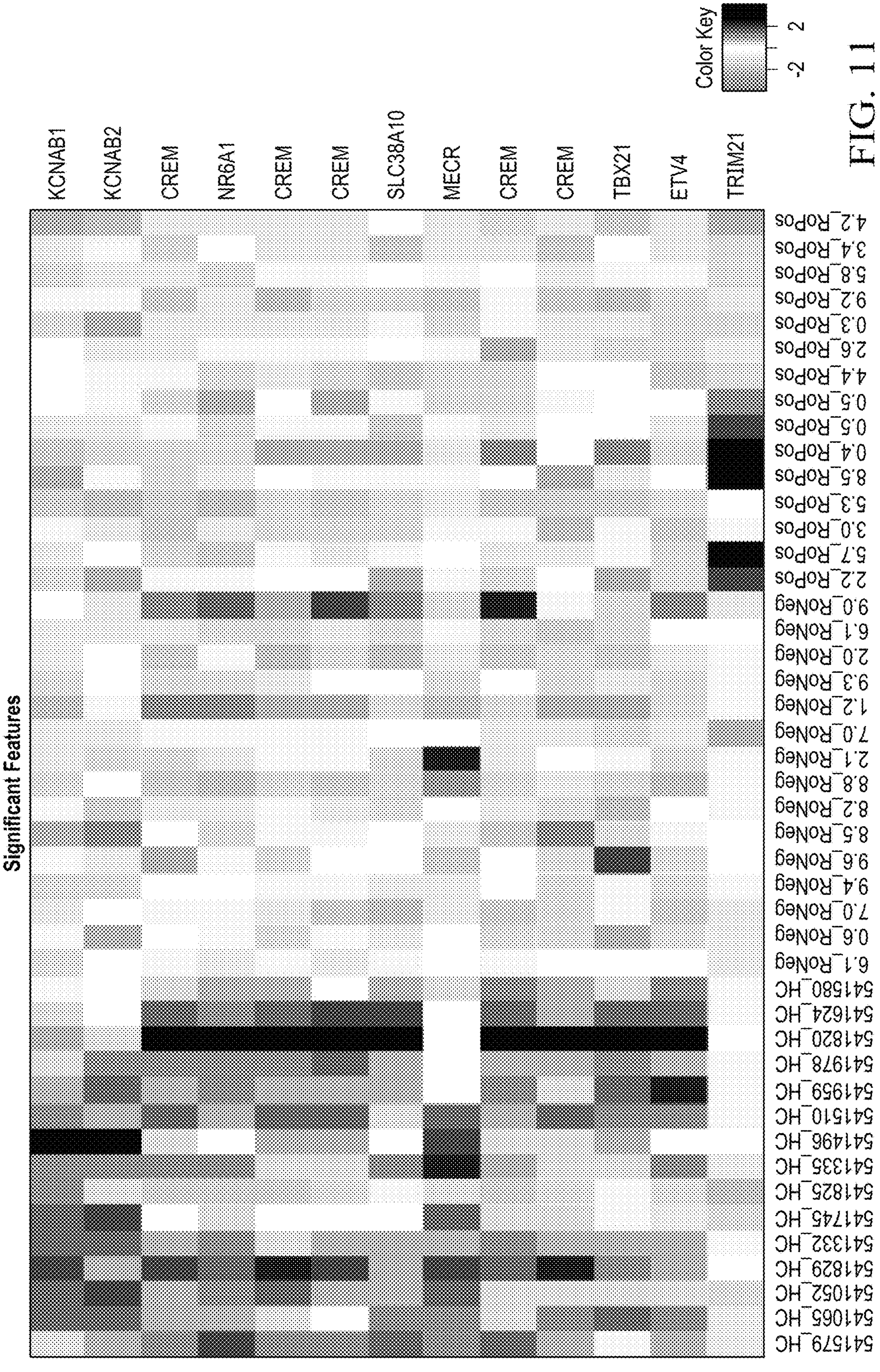
FIG. 11 is a table that shows the significant features reaching qValue<0.05 differentiation threshold that discriminate between SS cases and healthy controls as assessed using the PAA Bioconductor package in R. A total of 9 proteins representing 13 separate features of the HuProt3.2 arrays significantly discriminated SS cases from healthy controls using a stringent significance threshold accounting for multiple comparisons.

FIG. 11 is a table that shows the significant features reaching qValue<0.05 differentiation threshold that discriminate between SS cases and healthy controls as assessed using the PAA Bioconductor package in R. A total of 9 proteins representing 13 separate features of the HuProt3.2 arrays significantly discriminated SS cases from healthy controls using a stringent significance threshold accounting for multiple comparisons.

Among these proteins, antibodies to KCNAB1 significantly discriminated between the Ro negative SS group and healthy controls, with antibody reactivity to KCNAB1 being significantly reduced in the SS cases. Evaluation of the magnitude of antibody binding to KCNAB1 in the three subject groups by Mann-Whitney U-test is shown in FIG. 12.

Figure 12:
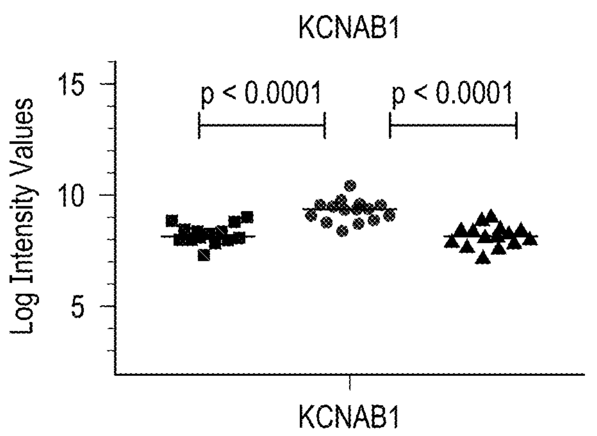
FIG. 12 is a graph that shows binding of KCNAB1 protein by healthy controls (circles, center) but not Ro negative SS cases (squares, left) or Ro positive SS cases (triangles, right). P-values using two-tailed Mann-Whitney U tests compared to the healthy control group are shown.

FIG. 12 is a graph that shows binding of KCNAB1 protein by healthy controls (circles, center) but not Ro negative SS cases (squares, left) or Ro positive SS cases (triangles, right). P-values using two-tailed Mann-Whitney U tests compared to the healthy control group are shown.

As antibodies to KCNAB1 were reduced in both anti-Ro positive and anti-Ro negative SS cases, the two SS patient groups were combined and compared to the healthy controls. The results are shown in FIG. 13.

Figure 13:
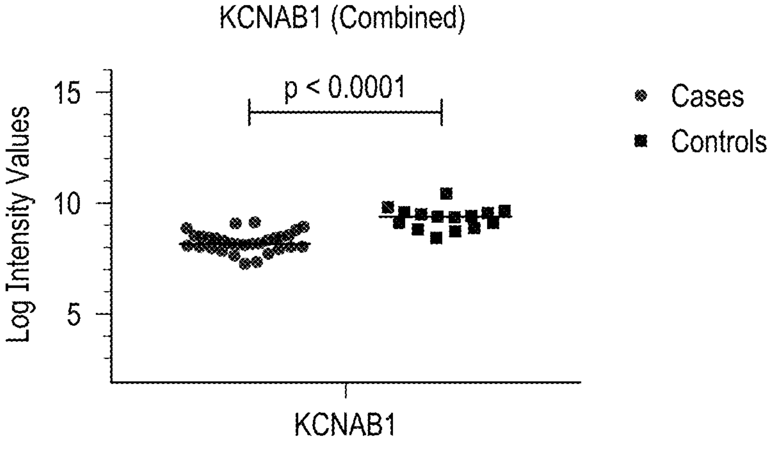
FIG. 13 is a graph that shows binding of KCNAB1 protein by the combined Ro positive and Ro negative SS cases (circles, left) compared to healthy controls (squares, right). The p-value shown reflects a two-tailed Mann-Whitney U test.

FIG. 13 is a graph that shows binding of KCNAB1 protein by the combined anti-Ro positive and anti-Ro negative SS cases (circles, left) compared to healthy controls (squares, right). The p-value shown reflects a two-tailed Mann-Whitney U test.

Figure 14:
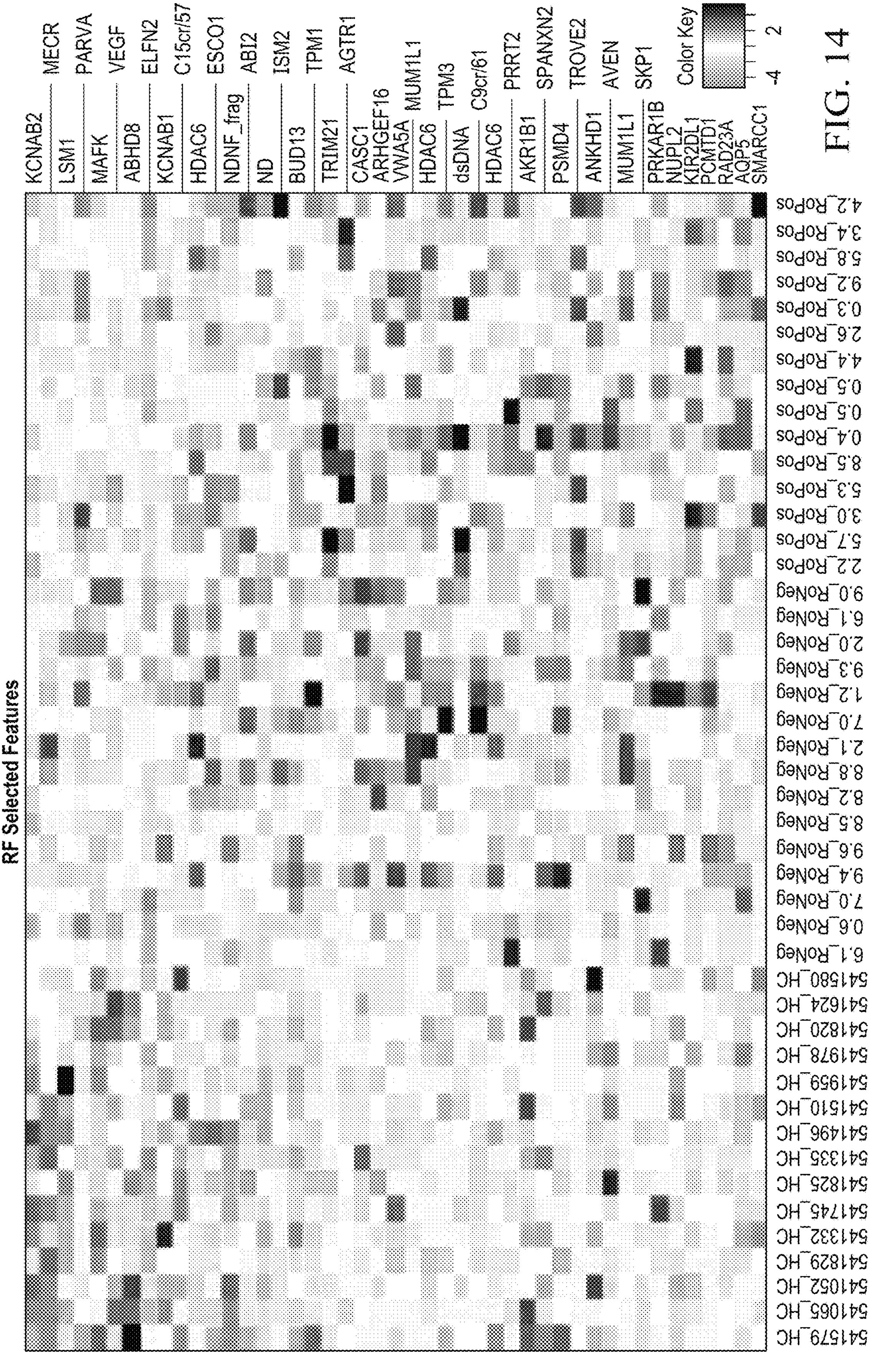
FIG. 14 shows a subset of 45 proteins selected by glmnet from a panel of 126 proteins identified by the multivariate RF-RFE approach as useful for discriminating between SS patient groups and healthy controls. Data reflect patient plasma IgG antibody binding to proteins on HuProt3.2 arrays. Analysis conducted using the PAA Bioconductor package in R.

Using the PAA Bioconductor package in R, the multivariate RF-RFE approach selected 126 proteins that discriminated between SS cases and healthy controls. Of these, 45 that were sub-selected with glmnet are shown in FIG. 14. These include KCNAB2, MECR, LSM1, PARVA, MAFK, VEGF, ABHD8, ELFN2, KCNAB1, C15orf57, HDAC6, ESCO1, NDNF_FRAG, ABI2, ND, ISM2, BUD13, TPM1, TRIM21, AGTR1, CASC1, ARHGEF16, VWA5A, MUM1L1, HDAC6, TPM3, dsDNA, c9ORF61, HDAC6, PRRT2, AKR1B1, SPANXN2, PSMD4, TROVE2, ANKHD1, AVEN, MUM1L1, SKP1, PRKAR1B, NUPL2, KIR2DL1, PCMTD1, RAD23A, AQP5 and SMARCC1 (for proteins, see genecards.org for full names).

FIG. 14 shows a subset of 45 proteins selected by glmnet from a panel of 126 proteins identified by the multivariate RF-RFE approach as useful for discriminating between SS patient groups and healthy controls. Data reflect patient plasma IgG antibody binding to proteins on HuProt3.2 arrays. Analysis conducted using the PAA Bioconductor package in R.

The entire list of 126 proteins identified as being useful for discriminating anti-Ro positive SS cases, anti-Ro negative SS cases and healthy controls is shown in Table 1.

TABLE 1

List of 126 proteins (or gene names encoding the proteins) identified by the PAA Bioconductor Package as being useful for discriminating Ro positive SS, Ro negative SS, and healthy

| | | | | |
|---|---|---|---|---|
| ABHD8 | EID3 | KCNAB1-1R49 | P2RX4 | SOX6 |
| ABI2 | ELFN2 | KIR2DL1 | PAIP1 | SPANXN2 |
| ACY1 | ERP27 | KIZ | PARVA | SRRT |
| AGTR1 | ESCO1 | LCN1 | PBK | STMN4 |
| AKRIB1 | FAF1 | LIPF | PCMTD1 | TCOF1 |
| ANKHD1 | FAM131B | LSM1 | PIK3CA | TEX29 |
| ANKRD45 | FAM131C | MAFK | PPP1R3F | TLK1 |
| AQP5 | FAM175B | MAG | PPP4R3A | TMED8 |
| ARHGEF16-R40 | FAM53C | MAPK8 | PRB1 | TMEM185B |
| ARHGEF16-R32 | GAB1 | MECR-R5 | PRKARIB | TPM1-R43 |
| AVEN | GAGE10 | MECR-R6 | PRRT2 | TPM1-R42 |
| BUD13 | GAR1 | MTMR14 | PSMD4 | TPM3 |
| C14orf37 | GBP5 | MUC20 | PTP4A1 | TRIM21** |
| C15orf57 | GCSH | MUM1L1-R24 | RAB34 | TROVE2*** |
| C9orf61 | GMPR | MUM1L1-R4 | RAD23A-R21 | TSC22D3 |
| CAAP1 | GNAS | NAF1 | RAD23A-R7 | TSSC4 |
| CASC1 | GORASP1 | NAT6 | RCC1 | VEGF |
| CAST | HDAC6-R14 | ND MIR16 | RTN4 | VWA5A |
| CCDC155 | HDAC6-28R20 | ND SIAT7D | SERPINB1 | WASF2 |
| CCER1 | HDAC6-20R20 | ND MTHFR | SFT2D2 | ZBTB7C |
| CYTH1 | HLCS | ND C20orf58* | SGIP1 | ZCCHC10 |
| DDX58 | HSPA13 | ND UBE3C | SKP1-R26 | ZEB2 |
| DNAJC12 | ISM2 | ND PTHB1 | SKP1-R6 | |
| dsDNA | KBTBD7 | NDNF_frag | SMARCC1 | |
| ECE1 | KCNAB1 | NFU1 | SMYD5_frag | |
| EEF1D | KCNAB2-16R49 | NUPL2 | SOX5 | |

*ND C20orf68 = FAM77A = NKAIN4;

TABLE 1-continued

List of 126 proteins (or gene names encoding the proteins) identified by the PAA Bioconductor Package as being useful for discriminating Ro positive SS, Ro negative SS, and healthy

**TRIM21 = Ro52 canonical SS antigen;

***TROVE2 = Ro60 canonical SS antigen.

Combinations of smaller subsets of the 126 proteins selected with the PAA Bioconductor multivariate RF-RFE approach may be useful for diagnosing Ro negative SS, as well as distinguishing Ro negative SS from healthy controls and Ro positive SS. An illustration of this is an example in which only 3 proteins, KCNAB2, CREM and TRIM21, could distinguish all three subject categories tested. This example is shown in FIG. 15.

Figure 15:
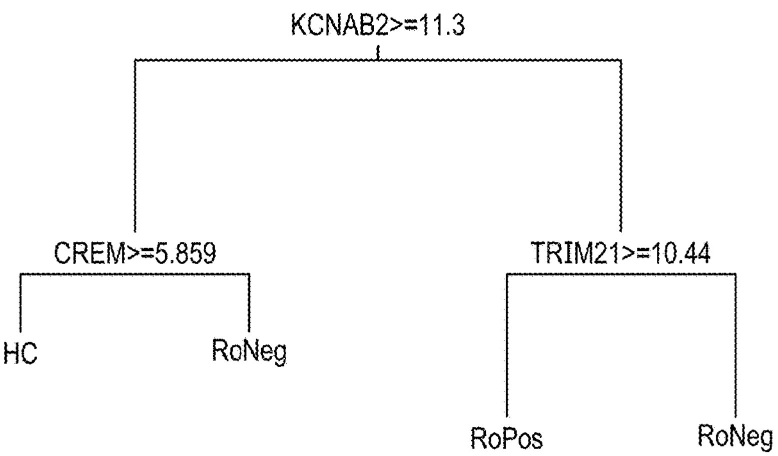
FIG. 15 shows one representative example showing how a subset of proteins identified by the PAA Bioconductor multivariate RF-RFE approach can distinguish Ro negative SS cases from Ro positive SS cases and healthy controls.

FIG. 15 shows one representative example showing how a subset of proteins identified by the PAA Bioconductor multivariate RF-RFE approach can distinguish anti-Ro negative SS cases from anti-Ro positive SS cases and healthy controls.

Sjögren's Syndrome is a debilitating disease, and the autoantibodies identified in these analyses represent potential biomarkers to aid in diagnosis and care of these patients. Furthermore, it could reduce the number of lip biopsies necessary, especially for the nearly 40% of patients that do not develop autoantibodies to the canonical Ro antigens.

Novel shared antibody specificities in anti-Ro antibody negative Sjögren's Syndrome.

Sjögren's syndrome (SS) is a rheumatic autoimmune disease characterized by focal lymphocytic infiltrates in the lacrimal and salivary glands, severe dry mouth and eyes, pain and debilitation. Diagnosis requires autoantibodies to ubiquitous Ro antigens or a lip biopsy positive for focal lymphocytic infiltrates. In this study, human proteome arrays were used to identify novel antibodies in plasma from Ro positive and Ro antibody negative SS patients compared with healthy controls.

Anti-Ro positive (n=15) and anti-Ro negative (n=15) cases meeting 2016 ACR/EULAR classification criteria for SS were age, race, and sex matched with each other and healthy controls (n=15) (15-15-15). Plasma IgG binding to human proteome arrays containing >19,500 recombinant human proteins representing >80% of the human proteome (HuProt v3.2 arrays, CDI Laboratories) was assessed. Data were normalized by the Robust Linear Model using the PAA Bioconductor Package in R and log intensity values for each protein generated. Thresholds of mean+3SD were established using the controls. Antigens bound by IgG in at least 4 cases compared to controls were considered significant ($p<0.05$, one-tailed Fisher's exact test).

IgG from anti-Ro positive SS cases significantly bound 42 proteins, including the canonical SS antigens Ro60, Ro52, and La, with an average of 15 specificities per individual. IgG from anti-Ro negative SS cases significantly bound 24 proteins compared to controls, with an average of 7 specificities per individual. Of the antigens identified, 8 were shared in both the Ro positive and Ro negative groups. Binding to at least one of these 8 proteins identified 93% of the Ro positive cases and 87% of the Ro negative cases.

A set of 8 novel antigens were bound by plasma IgG in both anti-Ro positive and anti-Ro negative cases. One or more of these antigens are used for diagnosing SS without a lip biopsy, including 1, 2, 3, 4, 5, 6, 7, or all 8 antigens or biomarkers.

TABLE 2

Proteins bound in 15-15-15 plasma above threshold of mean + 3SD of healthy controls.

| Ro Pos Name | ID | Ro Neg Name | ID | Shared Name | ID |
|---|---|---|---|---|---|
| AGTR1 | JHU16058.B8C25R46 | ARFGAP1 | JHU05382.B7C23R30 | CCDC155 | JHU09052.B9C16R21 |
| ATL2 | JHU07112.B7C25R49 | C9orf78 | JHU02218.B4C21R32 | DDB1 | JHU08569.B11C22R18 |
| CBX3 | JHU06273.B24C5R40 | CCDC155 | JHU09052.B9C16R21 | MUM1L1 | JHU15438.B17C15R24 |
| CCDC155 | JHU09052.B9C16R21 | CNDP2 | JHU02518.B1C4R41 | MUM1L1 | JHU15438.B18C27R4 |
| CPSF2 | JHU10483.B10C9R44 | DDB1 | JHU08569.B11C22R18 | NFU1 | JHU14404.B14C16R45 |
| DDB1 | JHU08569.B11C22R18 | FABP1 | JHU03967.B5C29R1 | RPS29 | JHU06790.B7C1R48 |
| dsDNA | auto-antigen | FXYD5 | JHU01290.B4C5R36 | SOX5 | JHU13672.B15C6R33 |
| EGFLAM | JHU12185.B15C31R8 | GRAMD1A | JHU07810.B9C8R2 | SOX5 | JHU06796.B8C19R46 |
| FAM118A | JHU09047.B11C25R21 | HNRNPAB | JHU08680.B9C25R18 | TCP10 | JHU10063.B12C3R42 |
| FUT3 | JHU11356.B9C24R57 | LIX1 | JHU03115.B21C10R42 | ZNF655 | JHU12825.B14C27R23 |
| FUT8 | JHU10594.B11C19R46 | MCCC2 | JHU04945.B8C31R14 | | |
| GAB1 | JHU09535.B23C26R51 | MUM1L1 | JHU15438.B17C15R24 | | |
| GMNN | JHU01959.B4C2R36 | MUM1L1 | JHU15438.B18C27R4 | | |
| HSFX1 | JHU01774.B19C26R47 | NFU1 | JHU14404.B14C16R45 | | |
| KLHDC8A | JHU05613.B8C24R28 | PEAS/ND | JHU00407.B3C12R10 | | |
| KRR1 | JHU01681.B23C25R42 | POU6F1 | JHU14773.B15C1R49 | | |
| MAPRE1 | JHU11847.B16C31R1 | PPIL3 | JHU11100.B9C13R50 | | |
| MCFD2 | JHU15435.B18C14R6 | RPAP3 | JHU07034.B5C14R53 | | |
| MUM1L1 | JHU15438.B18C27R4 | RPS29 | JHU06790.B7C1R48 | | |
| MUM1L1 | JHU15438.B17C15R24 | SOX5 | JHU13672.B15C6R33 | | |
| NFU1 | JHU14404.B14C16R45 | SOX5 | JHU06796.B8C19R46 | | |
| NUP50 | JHU09563.B12C30R28 | SPSB2 | JHU04978.B7C10R14 | | |
| PCMTD1 | JHU09086.B9C6R22 | SRPK2 | JHU16239.B19C22R17 | | |
| PDPK1 | JHU08321.B12C6R12 | TCP10 | JHU10063.B12C3R42 | | |
| PLEKHA4 | JHU16370.B18C7R13 | WDR20 | JHU01727.B24C18R40 | | |
| PLTP | JHU22252.B22C1R59 | ZNF655 | JHU12825.B14C27R23 | | |
| PML | JHU17186.B17C1R33 | | | | |
| POLR3H | JHU18583.B21C2R22 | | | | |
| POTEG | JHU25886.B24C2R70 | | | | |
| PRRG2/ND | JHU01414.B1C19R22 | | | | |
| PRRT2 | JHU07266.B6C10R53 | | | | |
| RAD23A | JHU16026.B17C31R7 | | | | |
| RCAN3 | JHU18309.B24C29R16 | | | | |
| RO52/ND | JHU00287.B2C16R4 | | | | |
| RPP38 | JHU26369.B24C3R70 | | | | |
| RPS29 | JHU06790.B7C1R48 | | | | |
| SEC23IP | JHU09577.B9C21R29 | | | | |
| SKIL | JHU07088.B19C25R40 | | | | |
| SOX13 | JHU10917.B11C27R52 | | | | |
| SOX5 | JHU13672.B15C6R33 | | | | |
| SOX5 | JHU06796.B8C19R46 | | | | |
| SOX6 | JHU06898.B6C31R48 | | | | |
| SOX6 | JHU06898.B22C25R37 | | | | |
| SSB | JHU18504.B22C28R13 | | | | |
| TCP10 | JHU10063.B12C3R42 | | | | |
| TNRC6C | JHU18133.B21C18R43 | | | | |
| TPI1 | JHU06136.B7C18R35 | | | | |
| TRAPPC8 | JHU06764.B7C24R46 | | | | |
| TRIM21 | JHU00287.B22C24R52 | | | | |
| TROVE2 | JHU06040.B5C11R35 | | | | |
| ZBTB16 | JHU19956.B23C12R65 | | | | |
| ZBTB46 | JHU12250.B15C28R10 | | | | |
| ZNF394 | JHU01440.B1C25R22 | | | | |
| ZNF655 | JHU12825.B14C27R23 | | | | |
| ZNF655_frag | JHU12919.B14C25R20 | | | | |

The column on left are proteins bound in the Ro Positive group. The middle column are proteins bound in the Ro Negative group. Protein Names/IDs highlighted in pink are shared between two groups, which are also listed in the columns on right.

Figure 16:
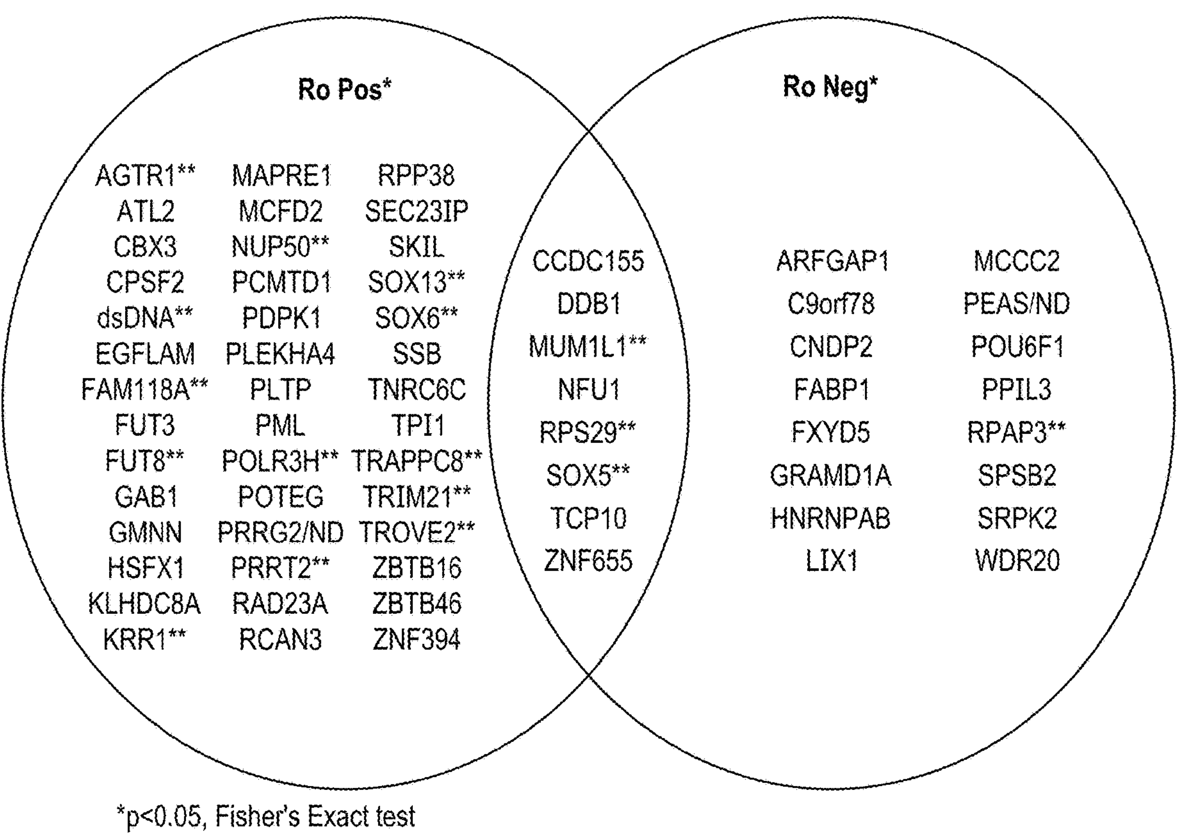
FIG. 16 is a Venn diagram that shows proteins bound in by plasma IgG among 15 anti-Ro antibody positive SS cases ("Ro Pos") and/or 15 anti-Ro antibody negative SS cases ("Ro Neg") above threshold of mean+3SD of plasma IgG among 15 healthy controls.

FIG. 16 is a Venn diagram that shows proteins bound in 15-15-15 plasma above threshold of mean+3SD of healthy controls. Duplicates were removed to save space, i.e. MUM1L1, SOX 5, SOX6, Ro52/ND (TRIM21 present) and ZNF655_frag (ZNF655 present). Proteins bound in 15-15-15 (Anti-Ro positive (n=15), anti-Ro negative (n=15) cases meeting 2016 ACR/EULAR classification criteria for SS were age, race, and sex matched with each other and healthy controls (n=15)) plasma above threshold of mean+3SD of healthy controls. *p<0.05, Fisher's Exact test, **bound with mean+4SD threshold.

TABLE 3

Plasma biomarkers overlapping between anti-Ro negative and anti-Ro positive patients.

| Protein marker | Full name, protein |
|---|---|
| CCDC155 | Coiled-Coil Domain Containing 155, UniProtKB: Q8N6L0 |
| DDB1 | Damage Specific DNA Binding Protein 1, UniProtKB: Q16531 |
| MUMIL1** | Melanoma Associated Antigen (Mutated) 1-Like 1, |

TABLE 3-continued

| Plasma biomarkers overlapping between anti-Ro negative and anti-Ro positive patients. | |
|---|---|
| Protein marker | Full name, protein |
| | UniProtKB: Q5H9M0 |
| NFU1 | NFU1 Iron-Sulfur Cluster Scaffold, UniProtKB: Q9UMS0 |
| RPS29** | Ribosomal Protein S29, UniProtKB: P62273 |
| SOX5** | SRY-Box Transcription Factor 5, UniProtKB: P35711 |
| TCP10 | T-Complex 10 Like 3, Pseudogene, UniProtKB: Q12799 |
| ZNF655 | Zinc Finger Protein 655, UniProtKB: Q8N720 |

**bound with mean + 4SD threshold

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited features, elements, components, groups, integers, and/or steps, but do not exclude the presence of other unstated features, elements, components, groups, integers and/or steps. In embodiments of any of the compositions and methods provided herein, "comprising" may be replaced with "consisting essentially of" or "consisting of". As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only. As used herein, the phrase "consisting essentially of" requires the specified features, elements, components, groups, integers, and/or steps, but do not exclude the presence of other unstated features, elements, components, groups, integers and/or steps as well as those that do not materially affect the basic and novel characteristic(s) and/or function of the claimed invention.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB. BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least #1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112. U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

1. Shiboski C H, Shiboski S C, Seror R, Criswell L A, Labetoulle M, Lietman T M, Rasmussen A, Scofield H, Vitali C, Bowman S J, Mariette X. 2017. 2016 American College of Rheumatology/European League Against Rheumatism Classification Criteria for Primary Sjogren's Syndrome: A Consensus and Data-Driven Methodology Involving Three International Patient Cohorts. Arthritis Rheumatol 69:35-45.

2. Shiboski C H, Shiboski S C, Seror R, Criswell L A, Labetoulle M, Lietman T M, Rasmussen A, Scofield H, Vitali C, Bowman S J, Mariette X. 2017. 2016 American College of Rheumatology/European League Against Rheumatism classification criteria for primary Sjogren's syndrome: A consensus and data-driven methodology involving three international patient cohorts. Ann Rheum Dis 76:9-16.
3. Maier-Moore J S, Koelsch K A, Smith K, Lessard C J, Radfar L, Lewis D, Kurien B T, Wolska N, Deshmukh U, Rasmussen A, Sivils K L, James J A, Farris A D, Scofield R H. Arthritis Rheumatol. 2014 December: 66 (12): 3445-56. doi: 10.1002/art.38872.
4. Rakhmanov M, Sic H, Kienzler A K, Fischer B, Rizzi M, Seidl M, Melkaoui K, Unger S, Moehle L, Schmit N E, Deshmukh S D, Ayata C K, Schuh W, Zhang Z, Cosset F L, Verhoeven E, Peter H H, Voll R E, Salzer U, Eibel H, Warnatz K. 2014. High levels of SOX5 decrease proliferative capacity of human B cells, but permit plasmablast differentiation. PLOS One 9: e100328.
5. Mingueneau M, Boudaoud S, Haskett S, Reynolds T L, Nocturne G, Norton E, Zhang X, Constant M, Park D, Wang W, Lazure T, Le Pajolec C, Ergun A, Mariette X. 2016. Cytometry by time-of-flight immunophenotyping identifies a blood Sjogren's signature correlating with disease activity and glandular inflammation. J Allergy Clin Immunol 137:1809-1821 e1812.
6. Jonsson M V, Skarstein K, Jonsson R, Brun J G. 2007. Serological implications of germinal center-like structures in primary Sjogren's syndrome. J Rheumatol 34:2044-2049.
7. Pei X H, Lv X Q, Li H X. 2014. Sox5 induces epithelial to mesenchymal transition by transactivation of Twist1. Biochem Biophys Res Commun 446:322-327.
8. Zhang D, Liu S. 2017. SOX5 promotes epithelial-mesenchymal transition in osteosarcoma via regulation of Snail. J BUON 22:258-264.
9. Leehan K M, Pezant N P, Rasmussen A, Grundahl K, Moore J S, Radfar L, Lewis D M, Stone D U, Lessard C J, Rhodus N L, Segal B M, Scofield R H, Sivils K L, Montgomery C, Farris A D. Clin Exp Rheumatol. 2018 May-June: 36 Suppl 112 (3): 80-88. Epub 2017 Oct. 23.
10. Edwards S K, Desai A, Liu Y, Moore C R, Xie P. 2014. Expression and function of a novel isoform of Sox5 in malignant B cells. Leuk Res 38:393-401.
11. Ramos-Casals M, Tzioufas A G, Font J. 2005. Primary Sjogren's syndrome: new clinical and therapeutic concepts. Ann Rheum Dis 64:347-354.
12. Fox R I, Kang H I. 1992. Pathogenesis of Sjogren's syndrome. Rheum Dis Clin North Am 18:517-538.
13. Guan Z, Dong B, Huang C, Hu X, Zhang Y, Lin C. 2019. Expression patterns of genes critical for SHH, BMP, and FGF pathways during the lumen formation of human salivary glands. J Mol Histol 50:217-227.
14. Yin H, Cabrera-Perez J, Lai Z, Michael D, Weller M, Swaim W D, Liu X, Catalan M A, Rocha E M, Ismail N, Afione S, Rana N A, Di Pasquale G, Alevizos I, Ambudkar I, Illei G G, Chiorini J A. 2013. Association of bone morphogenetic protein 6 with exocrine gland dysfunction in patients with Sjogren's syndrome and in mice. Arthritis Rheum 65:3228-3238.
15. Lessard C J, Li H, Adrianto I, Ice J A, Rasmussen A, Grundahl K M, Kelly J A, Dozmorov M G, Miceli-Richard C, Bowman S, Lester S, Eriksson P, Eloranta M L, Brun J G, Goransson L G, Harboe E, Guthridge J M, Kaufman K M, Kvarnstrom M, Jazebi H, Graham D S C, Grandits M E, Nazmul-Hossain A N M, Patel K, Adler A J, Maier-Moore J S, Farris A D, Brennan M T, Lessard J A, Chodosh J, Gopalakrishnan R, Hefner K S, Houston G D, Huang A J W, Hughes P J, Lewis D M, Radfar L, Rohrer M D, Stone D U, Wren J D, Vyse T J, Gaffney P M, James J A, Omdal R, Wahren-Herlenius M, Illei G G, Witte T, Jonsson R, Rischmueller M, Ronnblom L, et al. 2013. Variants at multiple loci implicated in both innate and adaptive immune responses are associated with Sjogren's syndrome. Nature Genetics 45:1284-1292.

What is claimed is:

1. A method of determining that a patient negative for anti-Ro autoantibodies has Sjogren's syndrome (SS) without performing a lip biopsy comprising:

obtaining a liquid biological sample from the patient;

detecting if the liquid biological sample has autoantibodies to 12, 3, 4, 5, 6, 7, 8, 9, 10, 11, 12, 13, 14, 15, 16, 17, 18, 19, 20, 21, 22, 23, 24, or 25 proteins selected from: RNA Polymerase II Associated Protein 3 (RPAP3), ADP Ribosylation Factor GTPase Activating Protein 1 (ARFGAP1), Chromosome 9 Open Reading Frame 7 (C9orf78), Carnosine Dipeptidase 2 (CNDP2), Fatty Acid Binding Protein 1 (FABP1), FXYD Domain Containing Ion Transport Regulator 5 (FXYD5), GRAM Domain Containing 1A (GRAMD1A), Heterogeneous Nuclear Ribonucleoprotein A/B (HNRNPAB), Limb And CNS Expressed 1 (LIX1), Methylcrotonyl-CoA Carboxylase Subunit 2 (MCCC2), POU Class 6 Homeobox 1 (POU6F1), Peptidylprolyl Isomerase Like 3 (PPIL3), Sp1A/Ryanodine Receptor Domain And SOCS Box Containing 2 (SPSB2), Serine/Arginine-Rich Protein-Specific Kinase (SRPK2), WD Repeat Domain 20 (WDR20), KASH Domain-Containing Protein 5 (CCDC155), Damage Specific DNA Binding Protein 1 (DDB1), Melanoma Associated Antigen (Mutated) 1-Like 1 Pseudogene (MUM1L1), NFU1 Iron-Sulfur Cluster Scaffold (NFU1), Ribosomal Protein S29 (RPS29), SRY-Box Transcription Factor 5 (SOX5), T-Complex 10 Like 3 (TCP10), or Zinc Finger Protein 655 (ZNF655), wherein the level of autoantibody is ≥3 standard deviations (SD) above the mean of healthy controls;

determining that the patient is positive for the two or more of the autoantibodies above a mean of a healthy control; and administering to the patient negative for Ro autoantibodies with a therapy that treats or reduces the symptoms of SS.

2. The method of claim 1, further comprising at least one of:

detecting if the biological sample from the Ro negative patient has autoantibodies to at least two of: CCDC155, DDB1, MUM1L1, NFU1, RPS29, SOX5, TCP10, ZNF655, or RPAP3 from the Ro negative patient;

detecting if the liquid biological sample from the Ro negative patient has autoantibodies to at least three of: CCDC155, DDB1, MUM1L1, NFU1, RPS29, SOX5, TCP10, ZNF655, or RPAP3; and detecting if the liquid biological sample from the Ro negative patient has autoantibodies to four or more proteins, other than MUM1L1 and SOX5;

wherein if the liquid biological sample from the Ro negative patient has at least one of the above combinations of autoantibodies administering to the patient negative for Ro autoantibodies a therapy that treats or reduces the symptoms of SS.

3. The method of claim 2, wherein the autoantibody is ≥4SD above the mean of healthy controls and is to at least two of: MUM1L1, RPS29, SOX5 or RPAP3 to identify three-fourths of the Ro negative individuals with SS; the autoantibodies to SOX5 also cross-react with at least one of SOX3, SOX4, SOX6, SOX9, SOX11, SOX13 and SOX30; or both.

4. The method of claim 1, wherein the autoantibodies are detected using an assay selected from at least one of: ELISA, flow cytometry, fluorimetry, microscopy, immunofluorescence, radioimmunoassay, immunoenzymatic assay, fluorescence activated cell sorting (FACS), differential display, representational difference analysis, microarray, multiplexed bead based assay, Western blotting, immunohistochemical staining, immunocytochemical staining, dot blots, or surface plasmon resonance detection.

5. The method of claim 1, wherein the liquid biological sample is selected from a saliva, a blood, a plasma, a serum, or a tear sample.

6. A method of determining that a patient negative for Ro autoantibodies has Sjögren's syndrome (SS) without performing a lip biopsy comprising:

obtaining a liquid biological sample from the patient suspected of having SS;

determining that the patient is negative for Ro autoantibodies;

detecting autoantibodies to 2, 3, 4, 5, 6, 7, 8, or 9 proteins selected from: CCDC155, DDB1, MUM1L1, NFU1, RPS29, SOX5, TCP10, ZNF655, or RPAP3, in the liquid sample, wherein the presence of autoantibodies indicates that the patient has SS;

determining that the patient is positive for the two or more of the autoantibodies above a mean of a healthy control; and administering to the patient negative for Ro autoantibodies with a therapy that treats or reduces the symptoms of SS.

7. The method of claim 6, further comprising at least one of: the step of detecting if the liquid biological sample has autoantibodies to 2, 3, 4, 5, 6, 7, 8, or 9 proteins selected from: CCDC155, DDB1, MUM1L1, NFU1, RPS29, SOX5, TCP10, ZNF655, or RPAP3;

the step of detecting if the liquid biological sample has autoantibodies to the two or more proteins other than MUM1L1 and SOX5; or the step of detecting autoantibodies in an assay selected from the group consisting of a Western blot, an ELISA, a radioimmunoassay (MA), an immunoprecipitation assay, an electrochemiluminescence assay, a chemiluminescence assay, a fluorescence assay, a microarray, a multiplex bead-based assay, a dot blot, or a surface plasmon resonance detection.

8. The method of claim 6, wherein the autoantibody is ≥2SD, ≥3SD, or ≥4SD above the mean of healthy controls and is to at least of two of: CCDC155, DDB1, MUMIL1, NFU1, RPS29, SOX5, TCP10, ZNF655 antigens in the Ro negative group to identify the Ro negative individuals as having SS; the autoantibodies to SOX5 also cross-react with at least one of: SOX3, SOX4, SOX6, SOX9, SOX11, SOX13 and SOX30; or both.

9. A method of determining that a patient negative for Ro autoantibodies has Sjögren's syndrome (SS) without performing a lip biopsy comprising:

obtaining a liquid biological sample from the patient suspected of having SS;

determining that the patient is negative for Ro autoantibodies;

detecting autoantibodies selected from: CCDC155, DDB1, MUMIL1, NFU1, RPS29, SOX5, TCP10, ZNF655, or RPAP3, wherein the presence present of autoantibodies to RPAP3 indicates that the patient has SS;

determining that the patient is positive for the autoantibodies above a mean of a healthy control; and administering to the patient negative for Ro autoantibodies with a therapy that treats or reduces the symptoms of SS.

* * * * *